US012651095B2

(12) United States Patent
Bergounioux et al.

(10) Patent No.: US 12,651,095 B2
(45) Date of Patent: Jun. 9, 2026

(54) METHOD FOR DESIGNING AND VALIDATING THE SHAPE AND POSITIONING OF A CANNULA FOR A PATIENT BY SIMULATING THE INSERTION INTO THE TRACHEA

(71) Applicants: ASSISTANCE PUBLIQUE—HOPITAUX DE PARIS, Paris (FR); UNIVERSITÉ DE VERSAILLES SAINT-QUENTIN-EN-YVELINES, Versailles (FR)

(72) Inventors: Jean Bergounioux, Le Kremlin Bicetre (FR); Marek Bucki, Theys (FR); Antoine Perrier, Ivry sur Seine (FR)

(73) Assignees: ASSISTANCE PUBLIQUE—HOPITAUX DE PARIS, Paris (FR); UNIVERSITE DE VERSAILLES SAINT-QUENTIN-EN-YVELINES, Versailles (FR)

( * ) Notice: Subject to any disclaimer, the term of this patent is extended or adjusted under 35 U.S.C. 154(b) by 1085 days.

(21) Appl. No.: 17/593,612

(22) PCT Filed: Mar. 26, 2020

(86) PCT No.: PCT/EP2020/058617
§ 371 (c)(1),
(2) Date: Sep. 21, 2021

(87) PCT Pub. No.: WO2020/193727
PCT Pub. Date: Oct. 1, 2020

(65) Prior Publication Data
US 2022/0171890 A1 Jun. 2, 2022

(30) Foreign Application Priority Data
Mar. 27, 2019 (EP) .................................... 19305391

(51) Int. Cl.
| G06F 30/10 | (2020.01) |
| A61M 16/04 | (2006.01) |
| G06F 30/23 | (2020.01) |

(52) U.S. Cl.
CPC ......... *G06F 30/10* (2020.01); *A61M 16/0434* (2013.01); *A61M 16/0463* (2013.01);
(Continued)

(58) Field of Classification Search
CPC .......... G06F 30/10; G06F 30/23; G06F 30/20; A61M 16/0434; A61M 16/0463; A61M 16/0465; A61M 2207/00; B33Y 80/00
See application file for complete search history.

(56) References Cited

U.S. PATENT DOCUMENTS 8,985,099 B2 * 3/2015 Freitag .............. A61M 16/0468
128/207.29
2012/0247473 A1 * 10/2012 Fendler ............. A61M 16/0427
128/205.27
(Continued)

FOREIGN PATENT DOCUMENTS

CN 105055060 A * 11/2015
FR 3042418 A1 4/2017

OTHER PUBLICATIONS

Kup-Sze Choi et al.; "A virtual reality based simulator for learning nasogastric tube placement"; Computers in Biology and Medicine 57 (2015) 103-115 (Year: 2015).*
(Continued)

*Primary Examiner* — Renee D Chavez
*Assistant Examiner* — Nupur Debnath
(74) *Attorney, Agent, or Firm* — Greer, Burns & Crain, Ltd

(57) ABSTRACT
A method for designing a cannula for a patient, wherein a processing unit is configured to implement following steps:
(Continued)

a) generating a 2D or 3D numerical representation of the trachea of the patient in at least one position,
b) identifying a set of anatomical landmarks,
c) considering a 2D or 3D numerical representation of a cannula based at least on the landmarks,
d) numerically simulating all or a part of an insertion of the cannula into the trachea,
e) estimating at least one reciprocal conflict metric between the cannula and the trachea during the insertion,
f) changing the cannula when the estimated conflict metric do not meet predetermined conflict criterion, and iterating at least one of the preceding steps until a cannula is found for which the estimated conflict metric meets the predetermined conflict criterion.

24 Claims, 5 Drawing Sheets

(52) U.S. Cl.
CPC ......... G06F 30/23 (2020.01); *A61M 16/0465* (2013.01); *A61M 2207/00* (2013.01)

(56) References Cited

U.S. PATENT DOCUMENTS

| | | | |
|---|---|---|---|
| 2014/0090194 A1* | 4/2014 | Stadelman | A61M 16/0463 15/104.05 |
| 2015/0258297 A1* | 9/2015 | Blom | A61M 16/0427 128/200.26 |
| 2018/0117219 A1* | 5/2018 | Yang | B29C 41/22 |

OTHER PUBLICATIONS

Subramaniam et al.; "How Design Characteristics of Tracheostomy Tubes Affect the Cannula and Tracheal Flows"; The Laryngoscope © 2018 The American Laryngological, Rhinological and Otological Society, Inc (Year: 2018).*
M. Kleine-Brueggeney et al.; "The performance of rigid scopes for tracheal intubation: a randomised, controlled trial in patients with a simulated difficult airway"; Anaesthesia 2016, 71, 1456-1463 (Year: 2016).*
A. Carter et al.; "The effect of inner tube placement on resistance and work of breathing through tracheostomy tubes: a bench test"; Anaesthesia 2013, 68, 276-282 (Year: 2013).*
Lee N Pryor et al.; "Tracheostomy Tube Type and Inner Cannula Selection Impact Pressure and Resistance to Air Flow"; Respiratory Care · May 2016 vol. 61 No. 5 (Year: 2016).*
International Search Report and Written Opinion received for PCT/EP2020/058617, mailed Jun. 17, 2020.
Extended European Search Report received in Application No. 19305391.5.
Kaye, R., et al., "Three dimensional printing: A review on the utility within medicine and otolaryngology," Journal of Pediatric Otorhinolaryngology 89, 2016, pp. 145-148.
Kleijn, B., et al., "Virtual 3D planning of tracheostomy placement and clinical applicability of 3D cannula design: a three-step study," European Archives of Oto-Rhino-Laryngology 275, 2018, pp. 451-457.
Müller, R., et al., "Development and first data of a customized short tracheal cannula based on digital data," Support Care Cancer 23, 2015, pp. 3089-3093.

* cited by examiner

Max= 1.44 mm

1

METHOD FOR DESIGNING AND VALIDATING THE SHAPE AND POSITIONING OF A CANNULA FOR A PATIENT BY SIMULATING THE INSERTION INTO THE TRACHEA

BACKGROUND

The present invention concerns a method for designing a cannula for a patient by generating a 3D numerical representation of the trachea of the patient in at least one position. The present invention relates to the technical domain of tracheotomy.

The tracheotomy is defined as a temporary aperture of the trachea held by a tube. The aperture closes at the withdrawal of the tube. This tube is commonly called cannula.

Tracheotomy can involve both children and adults. It can be used transiently or for a much longer duration and answers four indications: maintain the trachea open in case of obstruction, to be able to suction secretions in case of cough deficit, to protect false roads, and finally establish "prolonged" mechanical ventilation. All these tracheotomy indications are present in pediatric patients with neuromuscular disease.

The tracheotomy can be put in place by a surgical intervention or by a percutaneous insertion. This is a relatively simple procedure made by surgeons or anesthetists with a relatively low complication rate.

Tracheotomy induces several physiological changes which will be impacted by the cannula dimensions, shape and materials.

Tracheotomy will induce several physiologic modifications of ventilatory mechanics, effects on the tracheal wall, phonation, swallowing, humidification, orifice and aesthetics.

Concerning the ventilatory mechanics: tracheotomy has three distinct effects on ventilation: —an increase of resistances (related to internal diameter and length) which leads to an increase in spontaneous ventilation work with an increase of a peak expiratory pressure, —a decrease of anatomical dead space from 150 ml to 20 ml, which decreases minute ventilation and —an alteration of one of the cough times (closing of the glottis) which will impose tracheal suctioning.

Concerning the effects on the tracheal wall, tracheotomy may impair the "escalator" function of secretions of the mucosa (alteration of ciliary function), an ischemia by the pressure of the cannula balloon, cicatricial stenosis and progressive rise up the orifice due to positive pressures related to mechanical ventilation that tends to push up the cannula. The trachea is not a static organ but is constantly moving. These movements are linked to changes of patient position or simply to the breathing which induces translations of the tracheal walls in all directions. The introduction of the tracheotomy cannula, which is a non-compliant object with respect to the trachea, induces significant conflicts causing lesions at different levels of the trachea. These conflicts between the trachea and the material are responsible for much of the discomfort associated with tracheotomies and probably a significant part of accidental decannulation (the process whereby a tracheotomy cannula is removed once the patient no longer needs it). The epithelial and tissue lesions induced by said conflicts are the source of numerous mechanical or inflammatory complications of pseudotumoral type such as granulomas or stenoses. Part of the induced lesions requires endoscopic surgical treatment and may threaten patient's life.

Concerning the effects on the phonation, the tracheotomy does not affect the vocal cords or the larynx (phonatory apparatus). However, it can completely or partially suppress the expiratory flow through the phonatory apparatus. This is why several strategies exist to allow speech despite the cannula, but all must establish a flow above the tracheotomy. The main strategy is to make a window in the top of the curvature of the tracheotomy cannula to allow the air to take the path of the vocal cords. This requirement is rarely met because of the large anatomical variability that exists in patients. Windowing is therefore relatively rarely used because the pre-cut hole is regularly found facing the posterior tracheal wall and therefore not allowing the passage of air.

Concerning the effects on swallowing, the tracheotomy does not impair the swallowing function, which can be an argument for its realization (vs intubation). However, the cannula balloon may compress the esophagus and hinder the elevation of the larynx that may impair the swallowing sequence (which promotes micro-inhalation).

Concerning the effects on air humidification, the tracheotomy bypasses the nose, pharynx and larynx, which prevents humidification of the inspired air. In most cases, an artificial humidification is required, either by a heated humidifier or by a heat and humidity exchanger.

Concerning the effects on the cutaneous aperture, a permanent mature fistula may be developed in one week. This fistula may be stenosing or allow the development of granulomas making it difficult to introduce again a cannula. This patient-material conflict is partly related to the degree of disproportion between the cannula and the patient's anatomy.

Concerning the aesthetic aspect, it is well considered for long-term use. A specific approach to choose the cannula may be considered.

The dimensioning of a cannula.

The sizes of the tracheotomy cannulas are determined by their dimensions: inside diameter, outside diameter, length and curvature. The International Organization for Standardization (ISO) has determined these sizes in relation to the inside diameter of the cannula and the outside diameter at its anchor point.

A difference in the length of the tracheotomy cannula (tube) between cannulas of the same internal diameter has important clinical implications. The tracheotomy cannulas are bent or curved which can be used to improve the fit of the cannula in the tracheal duct. The shape of the cannula should be as consistent as possible with the anatomy of the airways. As the trachea is essentially straight, the curved cannula may not adapt to the shape of the trachea, which may result in compression of the membranous part of the trachea, while the tip of the cannula may traumatize the anterior part. The tracheotomy cannulas have generally a curved portion and a straight portion. They enter the trachea according to a small angle which allows less pressure on the stoma. The distal part of the cannula in the trachea is straight and more closely conforms to tracheal anatomy. The bent cannula can be centered in the trachea and exert less pressure on the tracheal wall.

Tracheotomy cannulas are made of several materials: silicone, polyurethane, acrylic, or PVC, in several diameters, in several lengths and in several curvatures. It is possible to order custom models but production times are long and prices are prohibitive. In the prior art, a custom cannula is assembled by technicians from silicone tubing which are glued together by biocompatible glues according to medical prescription.

Given the many aspects described above, tracheotomy can lead to complications as well as discomfort for the patient mainly due to the mechanical stresses applied to the tracheal wall by the cannula. This is particularly true in children and is manifested by bleeding, granulomas, hypersecretion, pain and sometimes accidental decannulation that can be fatal to the patient. Decannulations are all events that lead to an exit of the cannula from its tracheal location. They can be particularly serious when the patient is dependent on mechanical ventilation and does not have sufficient respiratory, neurological or muscular autonomy to put the cannula back in place, which is regularly the case in children with neuromuscular diseases. In this group of patients, this event is a constant risk and a significant cause of mortality. The causes of discomfort may be multiple and the discomfort felt due to a poorly adapted tracheotomy is an important element. The material-patient conflict of the extra-tracheal zone is also strongly implicated in discomfort, especially in children.

In order to produce custom cannulas, techniques exist to design cannulas in 3D. French patent application FR3042418, entitled "Tracheal intubation device", to BER-GOUNIOUX Jean; CARLIER Robert and PERRIER Antoine, discloses a tracheal intubation device comprising a cannula with a proximal portion outside the patient's body, a distal part for penetrating the trachea of the patient and a curved portion in the shape of an accordion hinge. The curved portion ensures the deformation of the cannula when the trachea deforms itself.

An object of the present invention is to provide a new method for designing a custom cannula.

Another object of the present invention is to provide a method for designing a cannula which can be maintained in the trachea with a high level of comfort. A further object of the present invention is to provide a method for designing a cannula which avoids lesions during the insertion in the trachea.

SUMMARY

At least one of the above-mentioned objects is achieved with a method according to the present invention for designing a cannula for a patient, wherein a processing unit is configured to implement following steps:

a) generating a 2D or 3D numerical representation of the trachea of the patient in at least one position,
  b) identifying a set of anatomical landmarks,
  c) considering a 2D or 3D numerical representation of a cannula based at least on said landmarks,
  d) numerically simulating all or a part of an insertion and/or a final positioning of the cannula into the trachea,
  e) estimating at least one reciprocal conflict metric between the cannula and the trachea,
  f) changing the cannula when the estimated conflict metric do not meet predetermined conflict criterion, and iterating at least one of the preceding steps until a cannula is found for which said estimated conflict metric meets the predetermined conflict criterion.

The present invention enables an automatic design of cannulas and the analysis of potential conflicts that are generated by these cannulas. It allows an estimation of the stability of the cannula and an assessment of the comfort felt by the patient.

To do this, the reciprocal conflict metrics are estimated through a dynamic and a static modelization processes.

The 2D or 3D representation allows reconstituting the patient's airways from 2D or 3D images. With landmarks, the specific morphology of the patient is taken into account. These landmarks provide geometric constraints that determine the shape, dimensions of the cannula and any points of contact with the trachea. Advantageously, the method according to the invention provides a dynamic analysis of the relationship between the cannula and the trachea. This analysis may include conflict analysis by simulation of insertion of the cannula. The dynamic analysis makes it possible to estimate conflict metrics which are then used by iteration to redefine the cannula: shape, dimensions, material (elasticity, etc.), . . .

In step c), during a first pass, the 2D or 3D representation can be generated without taking conflict metrics into account or by considering default values. When there are several iterations, we can start from step c) taking into account the conflict metrics calculated in step e) or we can start from step d) by performing a new simulation with a cannula modified at the step f). It is also possible to start directly from step e) by re-estimating the conflict metrics or else to apply step f) again by comparing the newly obtained conflict metrics after modification of the cannula.

By way of nonlimiting example, the simulation can in particular be implemented using the software Artisynth® or by means of commercial software such as those marketed by ANSYS®.

According to the invention, the method may further comprise a prior step of acquisition of morphological measurements by a static or dynamic medical imaging method, in at least one position of the patient.

The first step can be a CT (computerized tomography) scan of the tracheal anatomy while the patient is sitting and lying down. This scan is possible in any imaging service on a conventional scanner providing DICOM (Digital imaging and communications in medicine) files. The patient's airways are then for example reconstituted in 3D from the obtained DICOM files.

According to a preferred embodiment of the invention, the step d) may further comprise simulation of movements and positions of the patient. Thus, the simulation takes into account the movements of the patient preferably when the cannula is in its final position. Conflict metrics due to the movements of the trachea and surrounding organs are thus considered during the personalization of the cannula.

According to another embodiment of the invention, the step d) may further comprise a simulation of positioning of a cannula collar on the patient skin, said collar being intended to stay outside the trachea when the cannula is in the final position in the trachea. To do this, the representation of the trachea also includes a representation of the patient's skin in the region of interest.

In general, known cannulas may comprise a window realized in the bent part of the cannula in order to allow the passage of the air to the mouth. Such a window allows the patient to continue speaking despite the presence of the cannula. According to the invention, at the step c), landmarks may be used to automatically create a custom window in the cannula. Such a window according to the invention is therefore realized with a size, shape and position based on the morphology of the patient, ventilation needs and airflow necessary and sufficient to obtain a good quality of speech.

In general, known cannulas may comprise a balloon integrated in the cannula in order to prevent the passage of objects, food, saliva, aspiration accidentally coming from the pharynx to the lung. According to an advantageous feature of the invention, at the step c), landmarks may be used to automatically design and create a custom balloon of the cannula. Such a balloon is designed to take into account the conflict with the trachea when the balloon is inflated. To do this, the step d) may further comprise a simulation of an inflating of the balloon.

Preferably, the step c) further comprises generating a shape of the cannula from a median axis of the trachea obtained as a landmark at the step b).

Advantageously, as previously mentioned, at the step c), dimensions and/or shape and/or material of the cannula may be determined according to landmarks and conflict metric estimated at a previous iteration or based on default values.

According to an embodiment of the invention, the conflict metric estimation may be based on geometric calculations of interpenetration distances between the surface of the cannula and the surface of the trachea.

Such a first estimation of the reciprocal conflict metric based on geometric calculations quickly gives suitable results while requiring little computational effort.

According to the invention, for the geometric calculations, the surface of the cannula and the surface of the trachea may be supposed to be rigid. This is an assumption to simplify and accelerate the calculations.

According to another advantageous embodiment of the invention, the conflict metric estimation may be based on a biomechanical model of behavior using finite element models of both the trachea and the cannula.

A generic biomechanical model can be constructed and used as a reference. This model integrates—among other a priori knowledge—the tissues, organs and joints of the human body. For example, the biomechanical model is then transferred to the patient-specific 3D model using an anatomical transfer algorithm that deforms the shape of the generic model to accurately represent the patient's morphology.

A first assumption in the biomechanical model of the trachea could be either a rigid or a deformable solid.

Another assumption in the biomechanical model of the trachea could be a homogeneous and simplified isotropic rheology of the solid, or, conversely, heterogeneity and/or anisotropy of the tracheal tissues.

Preferably, another assumption in the biomechanical model of the trachea may include anatomical structures adjacent to the trachea, for example muscles, bones, ligaments, etc. Such a model combining soft tissues and musculoskeletal structures, allows a more realistic analysis of the conflict by taking into account the influence of the patient's movements on the stability of the cannula.

Advantageously, the biomechanical model may provide a numerical estimation of the magnitudes, directions and locations of contact forces between the cannula and the trachea. The contact forces may be estimated by means of an abacus relating these forces to geometrical measurements of interpenetration between 2D contours, or 3D surfaces.

Accordingly, the present invention relates to three types of conflict metrics:

geometrical conflict: interpenetration distance between rigid surfaces,
biomechanical conflict: contact pressures, mechanical stresses or contact stresses between deformable solids obtained by the Finite Element Method,
a hybrid solution: the conflict is based on an abacus which makes it possible to convert an interpenetration geometric calculation into an estimation of contact pressures.

For example, the conflict criteria are values in mm for geometrical conflict or mmHg for mechanical stresses.

At step b), the set of anatomical landmarks may comprise morphological data obtained from images acquired on the patient, and complementary data obtained from a statistical atlas of existing tracheas or inferred from machine learning techniques.

For example, three previous contours of the trachea under ultrasound tomography can be measured, and then a reconstitution of the 3D shape of the trachea using a statistical shape model can be done. Finally, to ensure proper shape inference, the shape can be validated, for example, by three, or more, other cuts under ultrasound tomography independent to the first one can then be done.

According to another embodiment of the invention, at step d), uncertainty analysis may be applied to an ideal insertion movement of a user and/or on the location of anatomical landmarks.

This analysis can be carried out by taking into account, during simulation, the uncertainties affecting the insertion motion of the cannula. These uncertainties are related to cannulation techniques, and/or location of anatomical landmarks on the patient. This means that the numerical simulation can adopt a probabilistic approach, for example using Monte-Carlo simulation method, where insertion simulations are explored by adding a controlled uncertainty to the insertion gesture rather than relying heavily on a movement of an ideal insertion, which ultimately is unlikely to be reproduced by a user.

According to another embodiment of the invention, the change in the step f) is to iterate the step c) by choosing a cannula from an existing library of cannulas or by automatically generating a numerical representation of the cannula modified according to the conflict metric estimated in a previous iteration with respect to the predetermined conflict criterion. The library could be a list of 2D or 3D representation of existing cannulas and their mechanical properties. Accordingly, the invention could be performed by iteratively simulating the insertion of existing cannulas and recording their mechanical properties.

According to another embodiment of the invention, the method may further comprise the step of generating data for producing the cannula in a 3D printing machine.

Advantageously, the method may further comprise the step of directly producing the cannula by 3D printing.

According to another aspect of the invention, the invention concerns a system for designing a cannula for a patient, said system comprising:

an imaging device for acquisition of morphological measurements by a static and/or dynamic medical imaging method, in at least one position of the patient,
a processing unit configured to implement the method as defined above, and
a 3D printing machine for producing the cannula.

The invention also concerns a non-transitory computer-readable storage medium encoded with computer-executable instructions which, when executed, perform a method as defined above.

BRIEF DESCRIPTION OF THE DRAWINGS

Further advantages and characteristics of the invention will become apparent on examining the detailed description of an embodiment, which is in no way limitative, and the attached drawings, in which:

FIG. 8.

DETAILED DESCRIPTION

Figure 1:
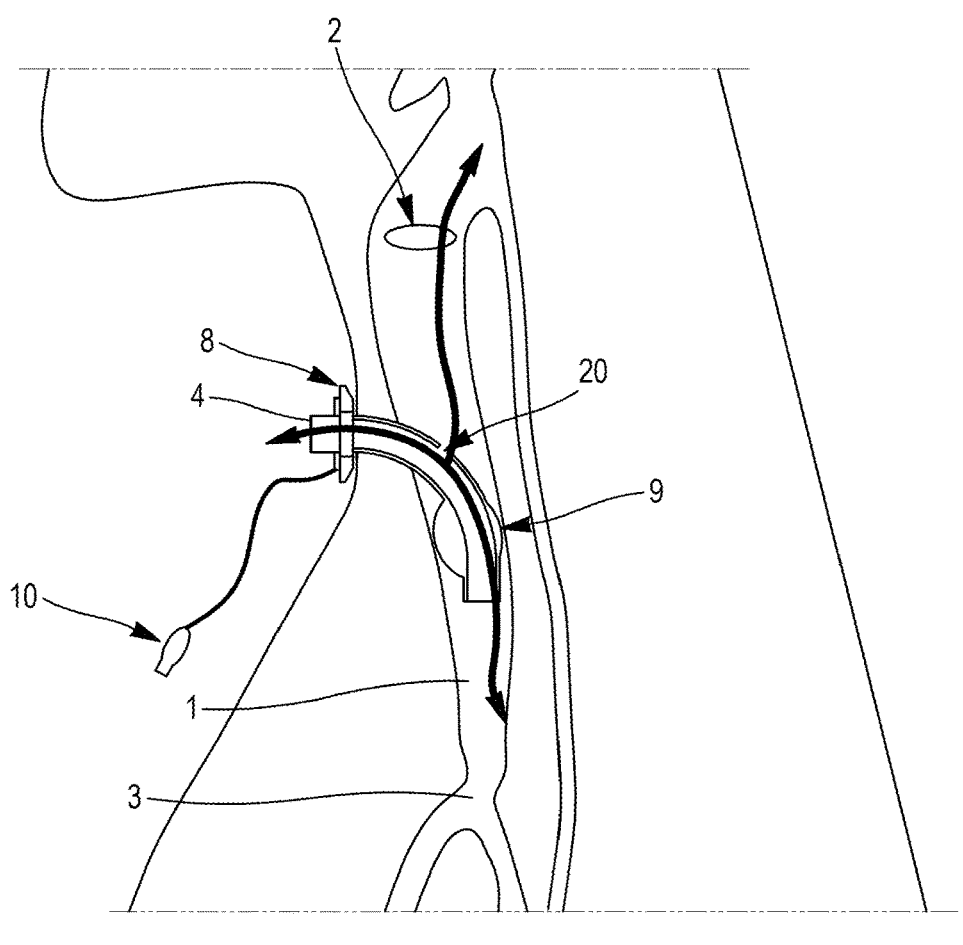
FIG. 1 is a schematic view of a cannula inserted inside a trachea of a patient.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the scope of the present invention as defined by the appended claims.

Hereinafter, the present invention will be described in detail by explaining exemplary embodiments of the invention with reference to the attached drawings. Like reference numerals in the drawings denote like elements.

The FIG. 1 schematically illustrates an upper part of a patient where the trachea 1 is a channel which leads vertically from the vocal cords 2 to the carina 3 of trachea.

The tracheotomy consists in realizing an aperture in the throat in order to insert a cannula 4 in the trachea.

Figure 2:
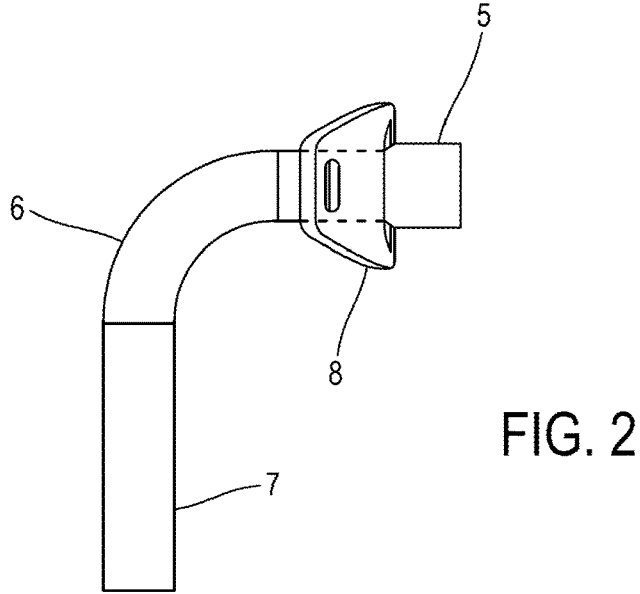
FIG. 2 is a schematic view of a cannula.

Cannula 4 is depicted on FIG. 2. It comprises three parts: a proximal part 5 which is intended to stay outside the patient, a curved part 6 which is intended to be internal to the patient making the link between the proximal part and a distal part 7 which is intended to be inside the trachea.

These three parts have the same internal and external diameter but different dimensions in terms of length.

The cannula 4 on FIG. 1 also comprises a collar 8 arranged around the proximal part 5 on FIG. 2. The collar 8, as depicted on FIG. 1, has the function of preventing the cannula to slide entirely inside the trachea. The collar 8 is intended to be in contact with the skin of the patient and holds the proximal part 5 outside the patient.

As illustrated on FIG. 1, a balloon 9 may be arranged around the distal part 7 of the cannula in order to create a sealing between the cannula and the internal wall of the trachea.

A pumping device 10 disposed outside the patient is available for the patient to inflate or deflate the balloon.

Figure 3:
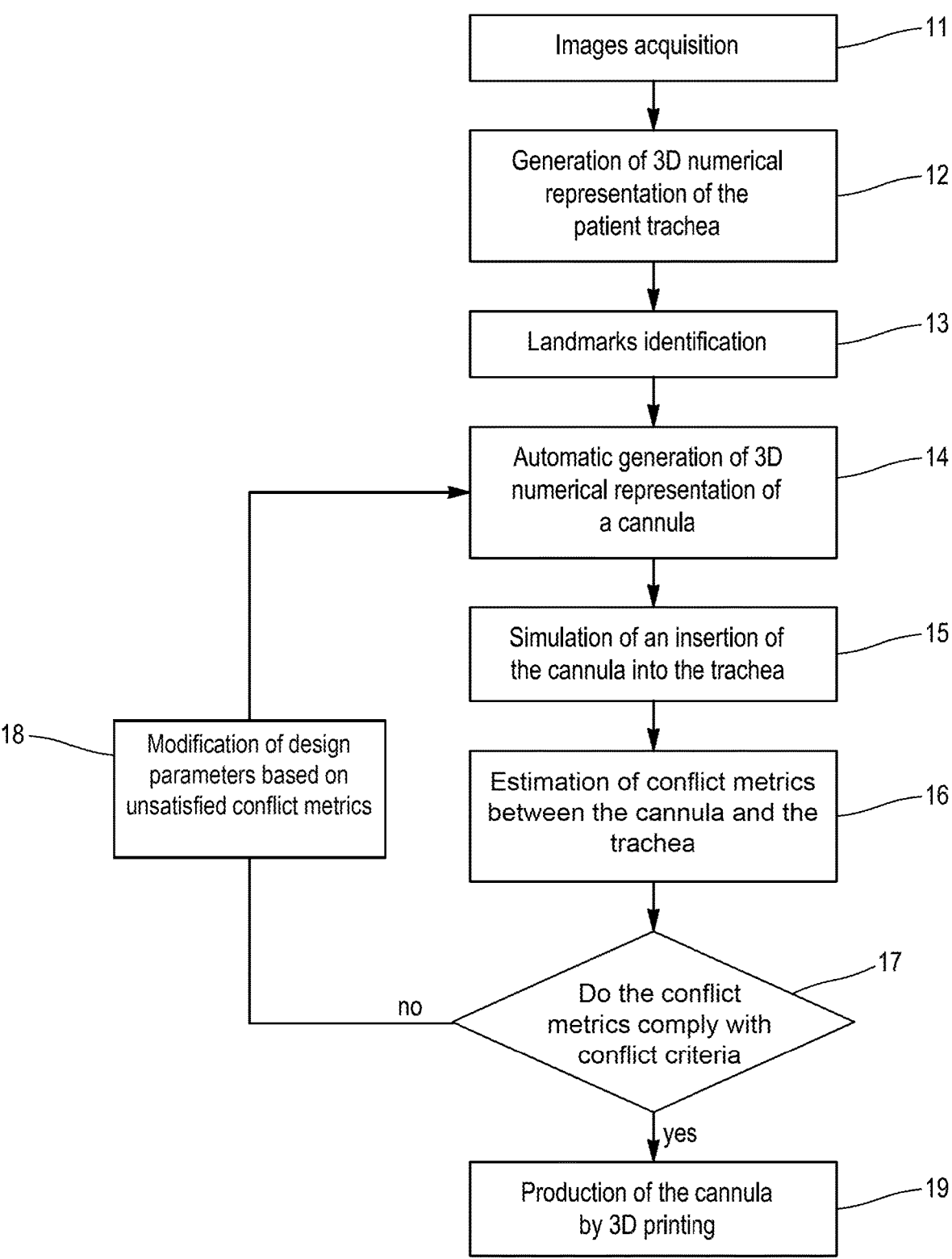
FIG. 3 is a graph illustrating different steps of a method for designing a cannula for a patient according to the present invention.

FIG. 3 illustrates different steps of an example of the method according to the invention. The present example is based on 3D representation but representations in lower dimensions are also possible. Moreover, all or a part of the steps herewith described may be embodied by a single device or by several devices located in different regions.

The step 11 concerns the acquisition of images of the trachea of the patient together with others organs around the trachea. At the step 12, a 3D numerical representation of the patient trachea is generated from the acquired images. Thus, the 3D numerical representation is a 3D model specific to the considered patient taking into account bone structures, cartilaginous structures, the trachea, as well as skin surface, in particular the conformance of the cannula collar with the patient's skin. The 3D models of the above-mentioned structures can be generated using a 3D surface reconstruction software.

In order to take into account the dynamic aspect of human body, a generic biomechanical model is used as reference. This generic biomechanical model integrates, among other structures of interest, the relevant joints of the human body.

According to the invention, the biomechanical model is then adapted to accurately represent the patient-specific 3D morphology using an anatomical transfer algorithm.

Based on step 13, landmarks are set on the 3d representation in order to distinguish different feature points of the trachea, said points concerning the area where the cannula has to be inserted, diameter of the trachea, length of the trachea, etc.

At step 14, a 3D numerical representation of a cannula is automatically generated based on landmarks defined in the 3D representation.

Then, according to the invention, at step 15, appropriate software is used to simulate the insertion of the generated cannula in the trachea of the patient. The movement of the patient integrating this cannula is also simulated.

It is also possible to simulate movements of the patient when the cannula is installed, in the rest position, in the trachea.

The simulation step makes it possible to identify conflicts and to estimate conflict metrics, including metrics related to design constraints and/or mechanical constraints, between the cannula and the trachea at the step 16. Each conflict is automatically analyzed and the cannula is modified consequently. The modification may concern the dimension, the shape and/or the material constituting the cannula.

At step 17, a fit test is performed: do the conflict metrics comply with predetermined conflict criteria? If the response is yes, the cannula is then manufactured by 3D printing at step 19. But it is also possible to avoid the manufacturing, the cannula may be chosen from a library containing several predesigned cannulas of manufacturers provided that the generated cannula is included in the library. It is therefore an off-the-shelf cannula.

It may be considered to choose a cannula in the library which is not exactly the one numerically generated but a cannula presenting an acceptable difference.

If the response is "no" at step 17, by iteration, the cannula is then modified taking into account unsatisfied conflict metrics of step 18. The iteration is performed until a generated cannula complies with predetermined conflict criteria.

Reference will now be made to FIGS. 4 to 9 in order to describe in detail a non-limitative example of each step of FIG. 3.

Concerning the 3D Representation of the Trachea, Based on Steps 11 and 12.

The first step is a CT (computed tomography) scan of the tracheal anatomy while the patient is in sitting and lying down positions in order to generate DICOM (Digital imaging and communications in medicine) files. This acquisition is possible in any imaging service on a conventional scanner. The patient's airways are reconstituted in 3D from the obtained DICOM files.

Figure 4:
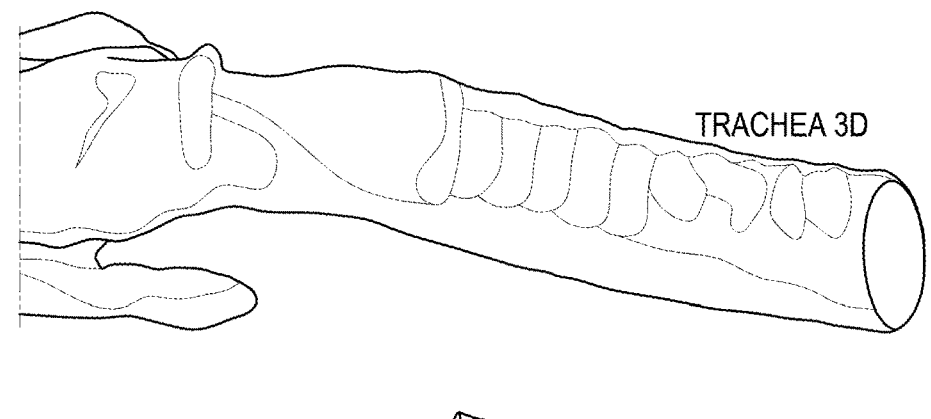
FIG. 4 is a schematic view of a 3D representation of the trachea along with its Region of Interest (ROI)
Figure 4:
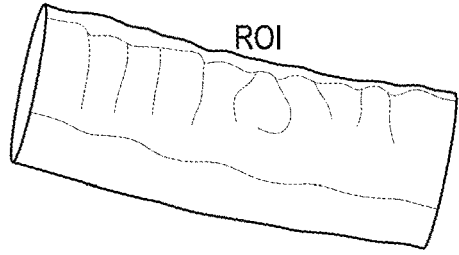

FIG. 4 illustrates a 3D representation of the trachea of a patient. A region of interest (ROI) may be defined as a tube of the trachea where the cannula is intended to be positioned. Concerning the Identification of Landmarks, Based on Step 13.

Figure 5:
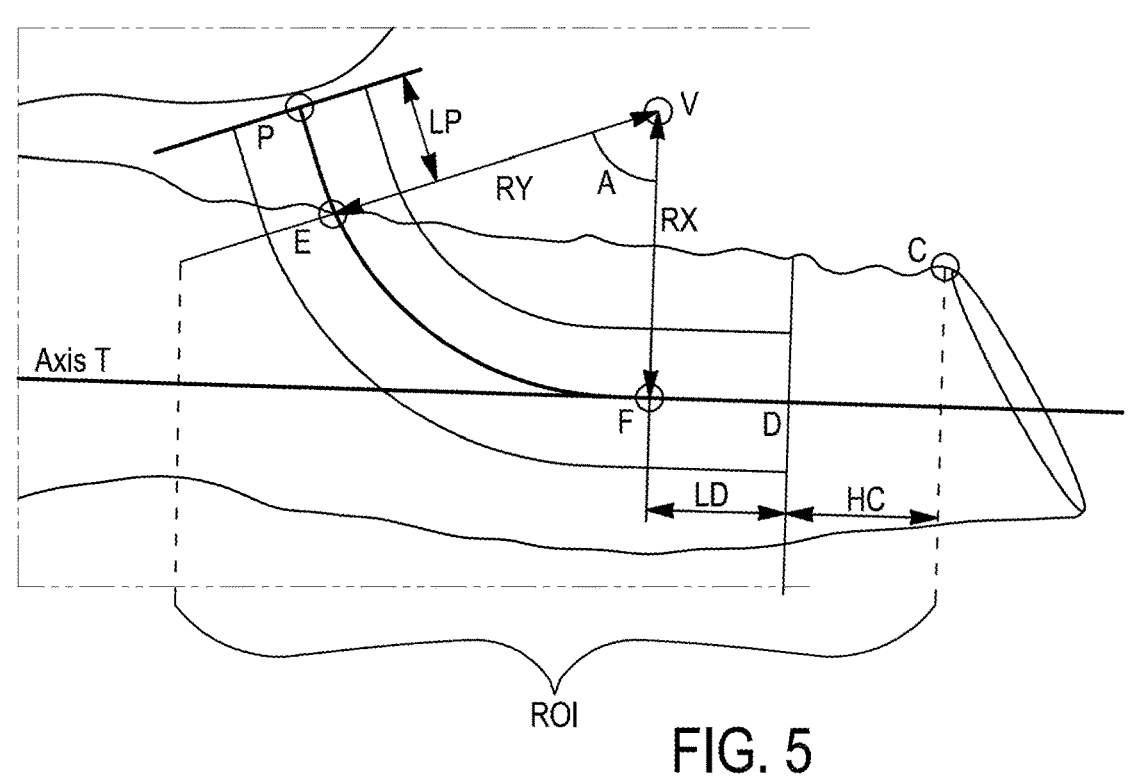
FIG. 5 is a schematic illustration of landmarks/axes and reference points to design a custom cannula with respect to data obtained by 3D reconstruction.

Reference is now made on FIG. 5 where landmarks are identified on the trachea representation. The landmarks are made with respect to different parts of the cannula.

The design of the proximal part of the cannula will be based on following landmarks: the proximal part of the cannula will be defined by a point of entry into the trachea located between the second, third or fourth tracheal ring according to the usual surgical references, point E, FIG. 5. The choice of a length of the proximal part will be determined by the shortest distance between the skin and the anterior tracheal wall measured on the 3D reconstruction of the patient and measured along an axis at right angle to the cutaneous surface, distance LP, axis PE, FIG. 5. The length of this first segment PE will be adjusted to the eventual variation of the distance LP following the posture change of the patient. The angle of this axis PE with the trachea axis T can vary by a maximum of +/−60° according to dynamic considerations. The length LP of the proximal part will be measured with a variation of length of +/−2 cm according to dynamic considerations.

The design of the distal part of the cannula will be based on following landmarks: the distal part starts at point D where the cannula's central axis overlaps the tracheal axis, or axis T, allowing the alignment of this distal part with axis T. The length of the distal part may vary from 0 cm at a distance that corresponds to that between point D and point F, which corresponds to the more proximal portion of the carina 3 on the FIG. 1. Distance CD will never be less than 0.5 cm and its best suitable length will be defined from static and dynamic considerations extracted from the patient anatomy.

There is a relationship between the angle A of the cannula, and the length of the distal part LD. Indeed the more the angle is open (>120°), the longer the distal part LD must be, thus making it possible to stabilize the cannula during cervical movements or coughing efforts. The length may also depend on the particular anatomy of the trachea which can be circumvented and not rectilinear in these first centimeters.

The design of the radial part of the cannula will be based on following landmarks: The radial part starts at the point E and ends at the point F. This part is characterized by a regular curvature making it possible to pass from the axis P-E to the axis T and connecting the proximal and distal parts. The design of the radial part depends from a combination of the static position of the cannula once in the final position as well as from the dynamic movement from outside the trachea to the final position. The design of the radial part is a compromise minimizing the mechanical conflicts of both sequences.

The determination of the median axis of the trachea, axis T, and its average radius, radius T, is based on following considerations. The median axis of the trachea, axis T, corresponds to the principal inertial axis of the trachea. In the case of a trachea with a nearly cylindrical shape, its principle axis is very close to the axis of the cylinder approximating the trachea. This characteristic justifies the positioning heuristic of the cannula which consists of aligning the distal part, linear, on this axis.

The automatic calculation of axis T is done in two stages. First, the region of interest of the trachea, ROI, is estimated from points E and C. For this purpose, the EC axis is constructed and then two planes, one passing through E and the other through C, and whose normal is collinear with the EC axis are determined. The region of interest ROI is then defined as the part of the inner surface of the trachea (reconstructed from medical imaging) between these two planes.

The ROI thus defined is represented by a discrete surface modeled by a triangular mesh. The median axis T is calculated from this mesh as the main axis of inertia of the triangulated surface. This calculation is made so that the axis T is invariable to local or global discretization changes (size of triangles). Thus, a principal component analysis is carried out on the cloud of points corresponding to the centers of gravity of triangles of the mesh, said points being weighted in the covariance matrix with the area of the associated triangle. Axis T is then the line passing through the center of gravity of these weighted points and therefore the direction is the first eigenvector of the covariance matrix (vector associated with the largest eigenvalue).

Figure 6:
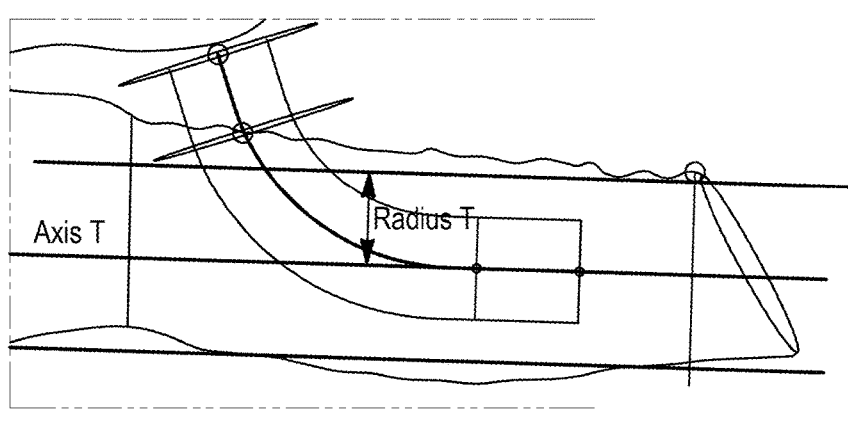
FIG. 6 is a schematic illustration of the definition of the trachea's axis and of its inner radius.
Figure 7:
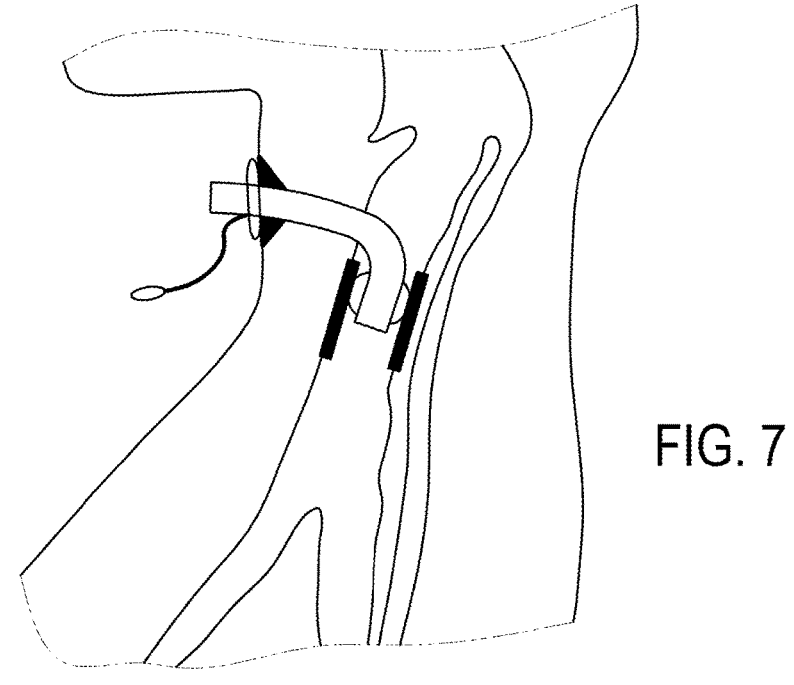
FIG. 7 is a schematic view of regions of conflict and lesions between the cannula of tracheotomy and the trachea.

On FIG. 6, once axis T is defined, the average radius, radius T, of the trachea is calculated as the average of the distances between axis T and the centers of each triangle of the ROI, again weighted by the area of the triangle.

Concerning the Automatic Generation of 3D Numerical Representation of a Cannula, Based on Step 14.

The steps of the cannula generation may be described as follows:

Calculation of the median axis of the trachea, axis T, and its average radius, radius T, Automatic determination of the shape and positioning of the cannula, Generation of the 3D shape of the cannula from the median axis.

The shape and positioning of the cannula generated by the algorithm takes into account the internal contours of the trachea (lumen), and the surface of the patient's skin. These two anatomical surfaces are reconstructed in 3D from medical images, as mentioned above.

The shape of the cannula is first defined by its median axis, whose calculation is based on the following data (FIG. 5):

The point of entry of the cannula into the tracheal lumen: point E. This point is situated between the second, third or fourth tracheal ring according to the usual surgical references;

The point of skin entry: point P. This point is calculated by the algorithm as the point on the skin surface of the patient, reconstructed in 3D, the closest to the point of entry E. The axis connecting the points P and E thus defines the orientation of the proximal part of the cannula, and the point P defines the final position of the cannula since the center of the collar is intended to rest at this point. The P-E axis forms a right angle with the anterior wall of the trachea. The angle of this axis with the trachea can vary by a maximum of +/−60° according to dynamic considerations. The length LP of the proximal part of the cannula is the distance between the point P and E;

The position of the carina: point C. This point is defined from the medical imagery of the patient. Located at the level of the fifth thoracic vertebra, it corresponds to the point where the trachea divides into both left and right stem bronchus. Point C defines the distal end of the region of interest (ROI) of the trachea;

The height HC may be defined by a user or automatically from predetermined parameters of the patient (for example size of the trachea, age of patient, etc.). It defines the height left between the distal end of the cannula D and the carina C. This height is measured along the median axis, axis T, of the region of interest (ROI) of the trachea.

From the median axis defined above, the 3D shape of the tube of the cannula is defined according to two parameters: first, the radius R of the tube of the cannula, which is supposed to be constant all along its median axis; then, the thickness EP of the cannula, which also does not vary along its length.

The radius R of the cannula can be determined automatically. It is possible to take its value within a tolerance interval defined by the user relative to the radius of the trachea radius. The thickness EP of the cannula can be determined by production constraints (minimum printable thickness) and/or optimized on the basis of numerical simulations, its value playing on the flexibility of the cannula.

These two parameters define an analytical shape of a tube which, in order to be represented by computer, must be discretized by a sampling method or a method of cutting into geometric primitives which are simple and exploitable on a computer.

The product of these samplings, called "mesh of the cannula" can take two forms with each a specific algorithmic aim.

The first discretization of the cannula generated by the algorithm is a finite element (FE) mesh whose finality is the mathematical simulation by the finite element method (FEM) of the mechanical behavior of the cannula in biomechanical interaction with the trachea. To do this, the FE mesh contains volumetric primitives (3D) or hexahedral "elements" (of generalized "cubic" form).

In order to generate the FE mesh, the sampling step along the median axis is chosen so as to satisfy a tradeoff between accuracy and speed of calculations. Indeed, a sampling step too fine leads to a mesh with too many finite elements, which considerably slows the calculations. On the other hand, a too big a step makes calculations faster but with of a loss of precision in the representation of the shape of the cannula. In view of the general profile of the cannulas, it is reasonable to choose a sampling step of the order or slightly less than one millimeter.

Given Sp the sampling step defined on the median axis of the cannula and expressed in millimeters. The set of sampling points is defined by the set of points P, E, F and D on FIG. 5, supplemented by intermediate points spaced at most every Sp millimeters. At each sampling point a Frenet trihedron is constructed by calculating at this point the following vectors:

the tangent to the median line of the cannula, obtained by derivation of the median line, a vector orthogonal to the median (sagittal) plan of the cannula. This plan is defined by the non-collinear points P, E, F and D.

a vector normal to the median line of the cannula, obtained by vector product of the two previous vectors.

The vector base thus formed constitutes a local Frenet trihedron at the sampling point considered. A discretization can be built every Sp millimeters of the ring of hexahedral elements of thickness EP, centered on the current sampling point, and of external radius R. The elements thus formed are slightly anisotropic in that they can have a base (in the angular plan) substantially square of Sp*Sp dimensions, and a different height (in the radial direction), EP. This, however, only affects the accuracy of calculations if EP is significantly different from Sp. In this case, the problem can be solved by subdividing the elements in the radial direction so as to produce a base/height ratio closest to 1.

The second discretization of the cannula generated by the algorithm is a so-called "surface" or "triangular" mesh. The purpose of this mesh is the 3D printing of the cannula produced by the software. In this type of meshes, the primitives used are surface (2D) and can be quadrilaterals or preferably triangles. The surface mesh immediately follows the mesh FE. It suffices to consider the external faces of the mesh FE i.e. all those which are not shared by two elements, then to cut these quadrilateral faces into triangles.

The numerical simulation of the behavior of the cannula using the mesh FE can then be realized.

Concerning the Simulation of an Insertion of the Cannula into the Trachea, Based on Step 15.

The present invention allows the minimization of conflicts between the cannula and the trachea (a) at the time of insertion; and (b) once the cannula is in place.

In order to simulate (a), the insertion movement of the cannula performed by the user should be reproduced numerically and as faithfully as possible. The configuration (b) is that obtained at the end of insertion movement.

The insertion movement of the cannula is simulated as follows.

A pivot point is chosen on the E-P segment. This point corresponds to the average tissue point around which the cannula rotates during the elbow. The movement of the linear sections, during the insertion thereof, is assumed to be a translation in the direction E-P.

Figures 8A, 8B, 8C, 8D:
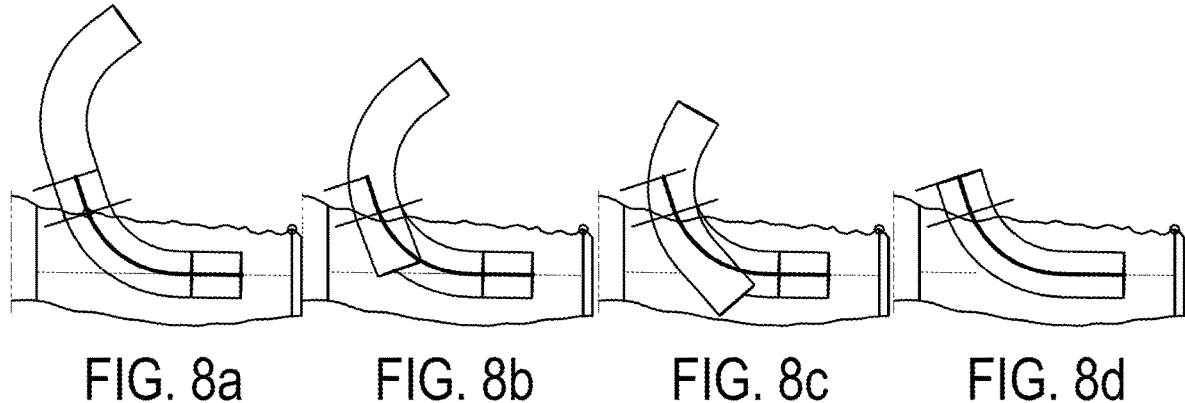
FIGS. 8a to 8d are four schematic views illustrating the decomposition of insertion movement.

Four stages of the insertion movement are shown on FIG. 8.

The solid line illustrates the cannula in the final position in the trachea, with a proximal part outside the trachea.

The pivot point chosen is the point E. On FIG. 8 a), the cannula is presented facing the point E of entry into the trachea, by superimposing its distal end D with the point E. On FIG. 8 b), the distal part is inserted whereas the distal point F of the cannula elbow, is superimposed on the point E. On FIG. 8 c), the elbow is halfway to the insertion. The point in the middle of the elbow is superimposed on the point E. On figure d) the cannula has reached its final insertion position.

The described example on FIG. 8 is based on a mathematical model where the insertion movement follows an ideal movement. This ideal movement assumes that the cannula swings around a fixed pivot center. Actually, the insertion movement performed by a user is not ideal as the cannula swings around a pivot center that moves. This is due to human intervention and the presence of friction between the cannula and the trachea, the skin and adjacent tissues. An inaccuracy in the center of the cannula leads to inaccuracy in calculating the conflict metrics. To control the inaccuracy, a sampled exploration of the various possible pivot points (located in the neighborhood of the E, P segment) can be made. The result of the conflict metrics estimation can then only retain the worst-case simulation (in a conservative approach), or a weighted result based on the assumption on a probabilistic distribution of pivot points between E and P (if the conservative approach excessively reduces the design options of the shape of the cannula for a given patient). The formulation of such a probabilistic distribution must be based on the experience of users and/or through experimentation on phantoms or anatomical parts.

Concerning the Estimation of the Cannula-Trachea Conflict Metrics, Based on Step 16.

At least two methods of calculation are possible in order to estimate quantitatively the conflict metrics between the cannula and the trachea during the insertion and once the cannula is in the final position.

The first method is a geometrical calculation of interpenetration distance between the surface of the cannula modeled in 3D, and the surface of the trachea reconstructed in 3D from medical imaging. The surfaces of the cannula and of the trachea are both considered rigid. The advantage of this calculation is its simplicity. Its limit is due to the fact that the deformations of the two structures during the insertion of the cannula are ignored.

The second method is based on a more complicated calculation to implement but more accurate. It is based on a biomechanical model.

The biomechanical estimation uses finite element modeling of the two structures, cannula and trachea.

Geometric Estimation of the Conflict.

Figure 9:
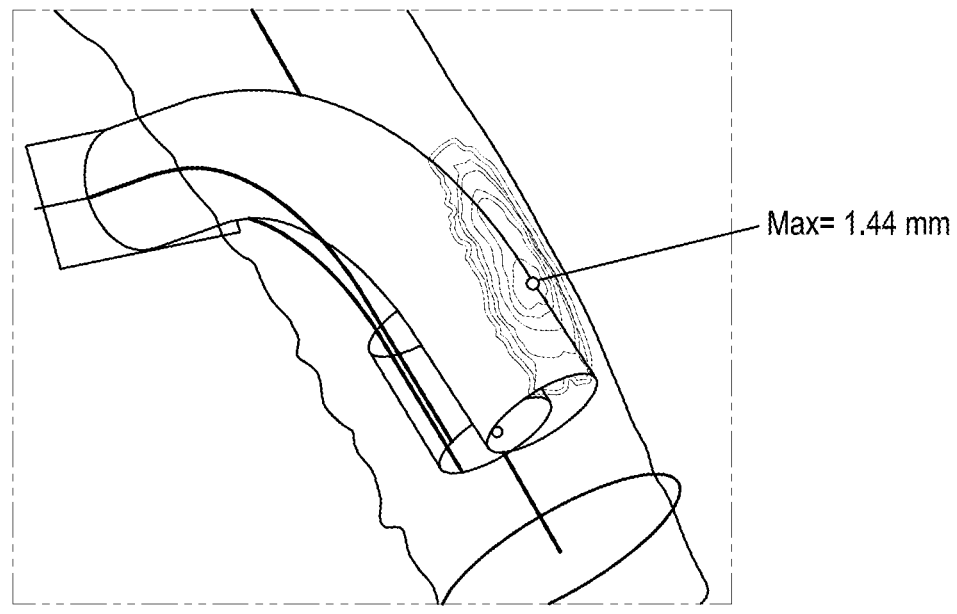
FIG. 9 is a schematic view illustrating a modeling of conflicts between the cannula and the internal wall of the trachea.

The geometric estimation of the conflict is displayed as a "collision map" on FIG. 9. The collision map is built on the ROI mesh and its values are updated at each step of the insertion of the cannula.

The collision value at a point on the map (i.e. at a vertex of the ROI), is the maximum value of the interpenetration distance between the 3D model of the cannula and the trachea (wall of the trachea and eventually organs next to the wall). On FIG. 9, for example, the maximum reached during the simulation of the insertion is 1.44 mm. A predetermined conflict criteria could be, for example, a maximum interpenetration threshold, expressed in millimeters.

This measurement is compatible with an exploration of uncertain parameters, such as the position of the pivot point during insertion. For this purpose, several insertion simulations can be performed and the maximum value at each point of the trachea that the cannula model crosses is retained on the collision map.

This calculation is visual, simple and fast but lacks realism due to the lack of consideration of deformations. However, it provides an order of magnitude of the conflict allowing the comparison of different cannula shapes. This calculation is especially based on the assumption that the maximum depth of collision of a cannula is proportional to the mechanical stresses that this cannula will exert on the wall during insertion. In particular, a cannula whose depth of penetration is zero, does not touch at any time the wall of the trachea, and naturally will not produce any mechanical constraint on it. The geometric method therefore offers a relative approximation of the conflict metric however less rigorously than the biomechanical estimation described hereafter.

Biomechanical Estimation of the Mechanical Stresses.

The calculation of the conflict between the cannula and the trachea by biomechanical simulation requires the implementation of the so-called finite element method (FEM). Resorting to FEM is more complex and requires more computation time than the geometric approach. This calculation, however, makes it possible to apprehend as accurately as possible the interactions between these two entities. The output of the geometric conflict calculation is a measurement of the interpenetration between two solids. By contrast, the biomechanical estimation of the conflict produces a different metric since it makes it possible to estimate the magnitude and directions of the contact forces between the cannula and the trachea.

Before dealing with conflict modeling, we can first focus on modeling the behaviors of each entity separately.

The cannula is a mechanical part whose materials and geometry are known. As already described, the method of construction of the finite element (FE) mesh is used for the implementation of the finite element method (FEM). By calculating the solution of a set of differential equations derived from the continuum mechanics, and the theory of solids elasticity in particular, the FEM makes it possible to predict the mechanical response (such as deformation, constraints or internal deformations) of the object modeled in response to external mechanical stresses (such as the application of displacement, pressure, torsion, etc.). Constitutive laws and rheological parameters that condition the mechanical behavior of the cannula are also used. These laws make it possible to establish a relation between the deformation of a solid and the forces necessary to produce it. The parameters themselves allow adjusting the behavior of these laws. An example to clarify this distinction: some biological tissues follow the same constitutive laws as the rubber used in the manufacture of tires but do not have the same rheological parameters. The trachea is a biological organ. To create a biomechanical model, 3D medical images of the shape of the trachea along with surrounding anatomical structures are acquired. Then a finite element mesh is constructed based on the 3D contours of the organs of interest extracted from these images.

During biomechanical modeling, assumptions may be made to reduce calculations. Different degrees of realism can be achieved by a biomechanical model of the trachea. For example, here are three examples of models, from the simplest to the most complex:

Model 1: the trachea is rigid solid or only "superficially deformable" (so-called "elastic foundation" model). In calculating the mechanical stresses, only the cannula undergoes significant deformations, governed by the most accurate mechanical model possible.

Model 2: the trachea is a deformable solid and the heterogeneity of its tissues and the possible anisotropy are taken into account.

Model 3: the trachea is a deformable solid, modeled by a mesh of finite elements of high resolution, and the adjacent structures (muscles, bones, ligaments, etc.) are also taken into account in the computation.

A model combining soft tissues and musculoskeletal structures, such as Model 3, allows an accurate analysis of the conflict by making it possible to study the influence of the patient's movements on the stability of the cannula.

Once the two biomechanical models of the cannula and of the trachea are determined, their behaviors can be combined in a common simulation to estimate the reciprocal mechanical stresses between the cannula and the trachea during a cannulation, and, preferably, during movements of the patient.

If at the end of the conflict simulation the result is unacceptable with respect to predetermined design constraints, such as a maximum contact pressure (expressed e.g. in mm of mercury (mmHg)), then the parameters of the shape of the cannula are corrected and the simulation restarts until the successive iterations converge to a cannula shape compatible with the trachea, static or dynamic, of the patient.

The parameters of the cannula shape can be optimized in a predefined range of acceptable values. The optimization of these parameters is based on the analysis of the geometrical or mechanical conflict between the cannula and the trachea. The following parameters, as depicted on FIG. 5, can be used:

the length of the distal segment LD corresponds to the length of the third section, rectilinear, of the cannula;

the shape of the elbow is defined so as to ensure a smooth transition between the proximal rectilinear section P-E and the distal section F-D.

On FIG. 5, the elbow is modeled by an elliptical arc defined by the following parameters:

first radius RX. This radius controls how far the cannula projects into the trachea. A correct positioning of the cannula should bring points F and D on the axis T.

second radius RY. This radius controls the rate at which the cannula plunges down the trachea.

the angular parameter A determines the amplitude of the elliptical arc between the points E and F. In the case of a circle, that is to say when RX=RY, A corresponds exactly to the angle between planes orthogonal to the median axis of the cannula at E and at F. In the case of an ellipse, that is to say when RX≠RY, A no longer corresponds to this angle due to the flattening of the elliptical arc.

the "virtual" point V is the center of the ellipse, whose spatial position is defined geometrically by the preceding parameters.

The elliptical arc has the advantage of accurately modeling the elbows of existing cannulas. It should be noted, however, that some configurations do not admit the existence of such an arc, in other words, there is not always an elliptical arc passing through the points E and F while the tangents at these points are respectively supported by the lines E-P and F-D. To circumvent this limitation it is possible to use other parametric curves, such as "splines", to model the median elbow of the cannula. The shape of these curves can be deduced from the results of the insertion simulation of the cannula, so as to minimize the risk and/or discomfort for the patient.

Concerning the Production of the Cannula by 3D Printing, Based on Step 19.

The complete cannula is to be represented by a surface mesh (triangular) in order to be produced by 3D printing. However, the cannula comprises several elements such as the tube of the cannula, the collar, a connector for external tubing, an optional window, or fasteners for attaching a strap. A window 20 is depicted on FIG. 1. All of these elements must be combined into a single 3D object that will be subjected to printing. The sub-objects that make up the cannula may come from different sources. Indeed, if the shape of the cannula is produced by the algorithm according to the invention, some mechanical elements, such as the connector to the external tubing, may be drawn from CAD provided by a third party.

For assembling these different components, an algorithm called "Constructive Solid Geometry" (CSG), in its generalized form may be used.

In its simple form, the CSG produces new solids by applying Boolean operations between two 3D geometric primitives. The generalized CSG extends those Boolean operations to any closed solids. Let S1 and S2 be two three-dimensional solids, represented by a triangular mesh. The possible operations between these two solids can be:

the union: S=S1∪S2. The resulting solid S is a triangulated 3D surface corresponding to the union of the two volumes represented by S1 and S2.

the intersection: S=S1∩S2. The resulting solid S is a triangulated 3D surface corresponding to the intersection of the two volumes represented by S1 and S2.

subtraction: S=S1−S2. The resulting solid S is a triangulated 3D surface corresponding to the volume represented by S1 from which the volume of S2 has been subtracted.

According to the invention, the shape of the collar may be customized in order to optimize the stability of the inserted cannula and to maximize the comfort of the cannula. The proposed approach relies on the shape of the patient's skin near the skin insertion point P, as it is reconstructed in 3D from medical imaging.

One of the possible methods to achieve this result is as follows:

First of all, a bounding box of the collar is defined around the cutaneous insertion point P. The dimensions of this box define the width (left/right) of the collar, its height (up/down), as well as the maximum depth (front/back of patient) that it can take.

A triangular mesh of the bounding box is built with a discretization of the mesh which can be as rough as possible.

A generalized CSG subtraction is calculated between S1=bounding box and S2=skin of the patient. The result S=S1−S2 is the form of the collar perfectly congruent with the skin of the patient and contained in the dimensions of the bounding box specified beforehand.

The present invention concerns an improvement of tracheotomy tubes. To do this, the custom imaging and production facilities provided by the multi-strip scanner, 3D reconstruction application and 3D printing are advantageously used and allow a great progress in the tolerance and comfort of patients. Indeed, the present invention relates to a method of optimizing and verifying tracheotomy cannulas to allow their customized production after their design from a 2D/3D reconstruction of the patient's airways and a 2D/3D printing of the virtual model. The customization is accurate as the method takes into account the conflict between the cannula and the trachea including the surrounding organs. The conflict is estimated by means of reciprocal geometrical interpenetration or mechanical stresses. The cannula thus obtained, including the window, the collar and the balloon, is personalized with respect to the patient.

The invention claimed is:

1. A method for designing a tracheotomy cannula for a patient, wherein a processing unit is configured to implement following steps:

a) generating a 2D or 3D numerical representation of the trachea of the patient in at least one position;

b) identifying a set of anatomical landmarks;

c) considering a 2D or 3D numerical representation of a tracheotomy cannula based at least on said landmarks;

d) numerically simulating all or a part of an insertion of the tracheotomy cannula into the trachea, e) estimating at least one reciprocal conflict metric between the tracheotomy cannula and the trachea during the insertion; and f) when the estimated conflict metric does not meet predetermined conflict criterion, changing the tracheotomy cannula with respect to said estimated conflict metric, and iterating at least one of the preceding steps until a tracheotomy cannula is found for which said estimated conflict metric meets the predetermined conflict criterion.

2. The method according to claim 1, further comprising a prior step of acquisition of morphological measurements by a static or dynamic medical imaging method, in at least one position of the patient.

3. The method according to claim 1, wherein step d) further comprises simulation of movements and positions of the patient.

4. The method according to claim 1, wherein step d) further comprises a simulation of positioning of a tracheotomy cannula collar on the patient skin, said collar being intended to stay outside the trachea when the tracheotomy cannula is in the final position in the trachea.

5. The method according to claim 1, wherein at step c), landmarks are used to automatically create a custom window in the tracheotomy cannula.

6. The method according to claim 1, wherein at step c), landmarks are used to automatically create a custom balloon of the tracheotomy cannula.

7. The method according to claim 6, wherein step d) further comprises a simulation of an inflating of the balloon.

8. The method according to claim 1, wherein step c) further comprises generating a shape of the tracheotomy cannula from a median axis of the trachea obtained as a landmark at step b).

9. The method according to claim 1, wherein at step c), dimensions and/or shape and/or material of the tracheotomy cannula are determined according to landmarks and conflict metric estimated at a previous iteration or based on default values.

10. The method according to claim 1, wherein the conflict metric estimation is based on geometric calculations of interpenetration distances between the surface of the tracheotomy cannula and the surface of the trachea.

11. The method according to claim 10, wherein the surface of the tracheotomy cannula and the surface of the trachea are rigid.

12. The method according to claim 1, wherein the conflict metric estimation is based on a biomechanical model of behavior using finite element models of both the trachea and the tracheotomy cannula.

13. The method according to claim 12, wherein the biomechanical model of the trachea assumes either a rigid or a deformable solid.

14. The method according to claim 12, wherein the biomechanical model of the trachea assumes a homogeneous and simplified isotropic rheology of the solid, or heterogeneity and/or anisotropy of the tracheal tissues.

15. The method according to claim 12, wherein the biomechanical model assumes anatomical structures adjacent to the trachea.

16. The method according to claim 12, wherein the biomechanical model provides a numerical estimation of the magnitudes, directions and locations of contact forces between the tracheotomy cannula and the trachea.

17. The method according to claim 16, wherein the contact forces are estimated by means of an abacus relating these forces to geometrical measurements of interpenetration between 2D contours, or 3D surfaces.

18. The method according to claim 1, wherein at step b), the set of anatomical landmarks comprises morphological data obtained from patient acquired images and complementary predetermined data obtained from a statistical atlas of existing tracheas or inferred from machine learning techniques.

19. The method according to claim 1, wherein at step d), uncertainty analysis is applied to an ideal insertion movement of a user and/or on the location of anatomical landmarks.

20. The method according to claim 1, wherein the change in step f) is to iterate step c) by choosing a tracheotomy cannula from an existing library of tracheotomy cannulas or by automatically generating a numerical representation of the tracheotomy cannula modified according to the conflict metric estimated at a previous iteration with respect to the predetermined conflict criterion.

21. The method according to claim 1, further comprises the step of generating data for producing the tracheotomy cannula in a 3D printing machine.

22. The method according to claim 1, further comprises the step of producing the tracheotomy cannula by 3D printing.

23. A system for designing a tracheotomy cannula for a patient, the system comprising:
   an imaging device for acquisition of morphological measurements by a static and/or dynamic medical imaging method, in at least one position of the patient,
   a processing unit configured to implement the method according to claim 1, and
   a 3D printing machine for producing the tracheotomy cannula.

24. A non-transitory computer-readable storage medium encoded with computer-executable instructions which, when executed, perform a method according to claim 1.

* * * * *